United States Patent [19]

Cantello et al.

[11] Patent Number: 5,132,317
[45] Date of Patent: Jul. 21, 1992

[54] COMPOUNDS

[75] Inventors: Barrie C. C. Cantello, Epsom; Peter T. Duff, Reading, both of England

[73] Assignee: Beecham Group p.l.c., Middlesex, England

[21] Appl. No.: 571,734

[22] Filed: Aug. 23, 1990

[30] Foreign Application Priority Data

Aug. 25, 1989 [GB] United Kingdom ............ 8919434

[51] Int. Cl.$^5$ .................. A61R 31/425; C07D 277/34
[52] U.S. Cl. .................................. 514/369; 548/183
[58] Field of Search ................... 548/183; 514/369

[56] References Cited

U.S. PATENT DOCUMENTS 5,002,953  3/1941  Hindley .......................... 514/275

FOREIGN PATENT DOCUMENTS 0295828  12/1988  European Pat. Off. .
306228   3/1989  European Pat. Off. ............ 514/183
89/08650  9/1989  World Int. Prop. O. ........... 514/183

OTHER PUBLICATIONS

T. Sohda et al., "Studies on Antidiabetic Agents," *Chemical & Pharmaceutical Bull.*, vol. 30, No. 10, 3580-3600 (Oct. 1982).

*Primary Examiner*—Robert Gerstl
*Attorney, Agent, or Firm*—Hopgood, Calimafde, Kalil, Blaustein & Judlowe

[57] ABSTRACT

A compound of formula (I):

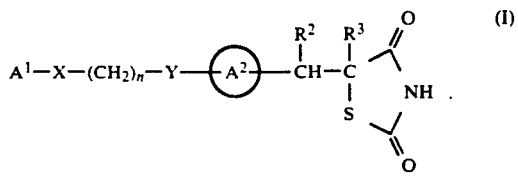

or a tautomeric form thereof and/or a pharmaceutically acceptable salt thereof, and/or a pharmaceutically acceptable solvate thereof, wherein:

$A^1$ represents a substituted or unsubstituted aryl group;
$A^2$ represents a benzene ring having in total up to five substituents;
X represents O, S or $NR^1$ wherein $R^1$ represents a hydrogen atom, an alkyl group, an acyl group, an aralkyl group, wherein the aryl moiety may be substituted or unsubstituted, or a substituted or unsubstituted aryl group;
Y represents O or S;
$R^2$ represents hydrogen;
$R^3$ represents hydrogen or an alkyl, aralkyl or aryl group or $R^2$ together with $R^3$ represents a bond; and
n represents an integer in the range of from 2 to 6; a process for preparing such a compound, a pharmaceutical composition comprising such a compound and the use of such compound and composition in medicine.

12 Claims, No Drawings

COMPOUNDS

This invention relates to certain substituted thiazolidinedione derivatives, to a process for preparing such compounds, to pharmaceutical compositions containing such compounds and to the use of such compounds and compositions in medicine.

European Patent Applications, Publication Numbers 0008203, 0139421, 0155845, 0177353, 0193256, 0207581, 0208420 and 0306228 relate to thiazolidinedione derivatives which are disclosed as having hypoglycaemic and hypolipidaemic activity. Chem. Pharm. Bull 30 (10) 3580–3600 also relates to certain thiazolidinedione derivatives having hypoglycaemic and hypolipidaemic activities.

It has now surprisingly been discovered that certain novel substituted-thiazolidinedione derivatives show improved blood-glucose lowering activity and are therefore of potential use in the treatment and/or prophylaxis of hyperglycaemia and are of particular use in the treatment of Type II diabetes.

These compounds are also indicated to be of potential use for the treatment and/or prophylaxis of other diseases including hyperlipidaemia, hypertension, cardiovascular disease and certain eating disorders.

Accordingly, the present invention provides a compound of formula (I):

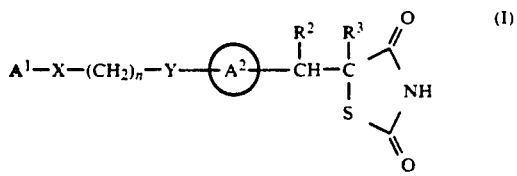

or a tautomeric form thereof and/or a pharmaceutically acceptable salt thereof, and/or a pharmaceutically acceptable solvate thereof, wherein:

$A^1$ represents a substituted or unsubstituted aryl group;

$A^2$ represents a benzene ring having in total up to five substituents;

X represents O, S or $NR^1$ wherein $R^1$ represents a hydrogen atom, an alkyl group, an acyl group, an aralkyl group, wherein the aryl moiety may be substituted or unsubstituted, or a substituted or unsubstituted aryl group;

Y represents O or S;

$R^2$ represents hydrogen;

$R^3$ represents hydrogen or an alkyl, aralkyl or aryl group or $R^2$ together with $R^3$ represents a bond; and n represents an integer in the range of from 2 to 6.

Favourably, $A^1$ represents a phenyl group.

Suitably $R^2$ represents hydrogen and $R^3$ represents an alkyl group, in particular a $C_{1-6}$ alkyl group, for example a methyl group.

Suitably, $R^2$ and $R^3$ each independently represent hydrogen.

Suitable substituents for the moiety $A^2$ include halogen, substituted or unsubstituted alkyl or alkoxy.

Favourably, $A^2$ represents a moiety of formula (a):

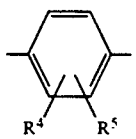

wherein $R^4$ and $R^5$ each independently represent hydrogen, halogen, substituted or unsubstituted alkyl or alkoxy.

Suitably, $R^4$ and $R^5$ each independently represent hydrogen, halogen, alkyl or alkoxy.

Preferably, $R^4$ and $R^5$ each represent hydrogen.

An example of X is O.

An example of Y is O.

In one preferred aspect the present invention provides a class of compounds, which fall wholly within the scope of formula (I), of formula (II):

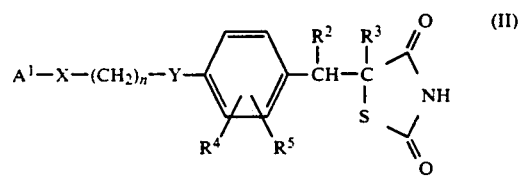

or a tautomeric form thereof, and/or a pharmaceutically acceptable salt thereof and/or a pharmaceutically acceptable solvate thereof, wherein $A^1$, X, Y, $R^2$, $R^3$ and n are as defined in relation to formula (I) and $R^4$ and $R^5$ are as defined in relation to formula (a).

Suitably, n represents an integer 2, 3 or 4, notably 2 or 3 and especially 2.

Suitably in the moiety $NR^1$, $R^1$ represents hydrogen, alkyl, acyl, especially acetyl, or benzyl.

Preferably in the moiety $NR^1$, $R^1$ represents a methyl group.

As indicated above a compound of formula (I) may exist in one of several tautomeric forms, all of which are encompassed by the present invention. It will be appreciated that the present invention encompasses all of the isomeric forms of the compounds of formula (I) and the pharmaceutically acceptable salts thereof, including any stereoisomeric forms thereof, whether as individual isomers or as mixtures of isomers.

When used herein the term 'aryl' includes phenyl and naphthyl, suitably phenyl, optionally substituted with up to five, preferably up to three, groups selected from halogen, alkyl, phenyl, alkoxy, haloalkyl, hydroxy, amino, nitro, carboxy, alkoxycarbonyl, alkoxycarbonylalkyl, alkylcarbonyloxy, or alkylcarbonyl groups.

When used herein the term 'halogen' refers to fluorine, chlorine, bromine and iodine; preferably chlorine.

When used herein the terms 'alkyl' and 'alkoxy' relate to groups having straight or branched carbon chains, containing up to 12 carbon atoms.

Suitable alkyl groups are $C_{1-12}$ alkyl groups, especially $C_{1-6}$ alkyl groups e.g. methyl, ethyl, n-propyl, iso-propyl, n-butyl, isobutyl or tert-butyl groups.

Suitable substituents for any alkyl group include those indicated above in relation to the term "aryl".

Suitable pharmaceutically acceptable salts include salts of the thiazolidinedione moiety, and, where appropriate, salts of amine groups or salts of carboxy groups.

Suitable pharmaceutically acceptable salts include metal salts, such as for example aluminium, alkali metal salts such as sodium or potassium, alkaline earth metal salts such as calcium or magnesium and ammonium or substituted ammonium salts, for example those with lower alkylamines such as triethylamine, hydroxyalkylamines such as 2-hydroxyethylamine, bis-(2-hydroxyethyl)amine or tris-(2-hydroxyethyl)amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine or quinoline.

In a further aspect the present invention also provides a process for the preparation of a compound of formula (I), or a tautomeric form thereof, and/or a pharmaceutically acceptable salt thereof, and/or a pharmaceutically acceptable hydrate thereof, which process comprises reacting a compound of formula (III):

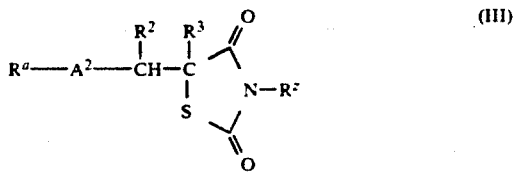

(III)

wherein $R^2$, $R^3$ and $A^2$ are as defined in relation to formula (I), $R^z$ is hydrogen or a nitrogen protecting group and $R^a$ is a moiety convertible to a moiety of formula (b):

$$A^1\text{-}X\text{-}(CH_2)_n\text{-}Y\text{-}$$ (b)

wherein $A^1$, X, Y and n are as defined in relation to formula (I), with an appropriate reagent capable of converting $R^a$ into the said moiety (b) and thereafter, if required, carrying out one or more of the following optional steps:

(i) converting a compound of formula (I) into a further compound of formula (I);

(ii) removing any protecting group;

(iii) preparing a pharmaceutically acceptable salt of the compound of formula (I) and/or a pharmaceutically acceptable solvate thereof.

Suitably, $R^a$ represents HY- wherein Y is as defined in relation to a compound of formula (I).

A compound of formula (III), wherein $R^2$ and $R^3$ each independently represent hydrogen or $R^2$ and $R^3$ together represent a bond, may be prepared from a compound of formula (IV):

(IV)

wherein $A^2$ is as defined in relation to the compound of formula (I) and $R^b$ is a moiety of formula $R^a$ or a moiety convertible into a moiety $R^a$, by reaction of the compound of formula (IV) with 2,4-thiazolidinedione; and thereafter, if required, converting a compound of formula (III) wherein $R^2$ together with $R^3$ represents a bond into a compound of formula (III) wherein $R^2$ and $R^3$ each represent hydrogen and/or converting a moiety $R^b$ into a moiety $R^a$.

The reaction between the compound of formula (IV) and 2,4-thiazolidinedione will of course be carried out under conditions suitable to the nature of the compound of formula (IV), in general the reaction being carried out in a solvent such as toluene, suitably at an elevated temperature such as the reflux temperature of the solvent and preferably in the presence of a suitable catalyst such as piperidinium acetate or benzoate. Favourably, in the reaction between the compound of formula (IV) and 2,4-thiazolidinedione, the water produced in the reaction is removed from the reaction mixture, for example by means of a Dean and Stark apparatus.

Suitably, $R^b$ represents $R^cY$- wherein Y is as defined above and $R^c$ is a protecting group, for example a benzyl group.

A compound of formula (III), wherein $R^2$ represents hydrogen and $R^3$ represents hydrogen, an alkyl, aralkyl or aryl group, may be prepared by reacting a compound of formula (V):

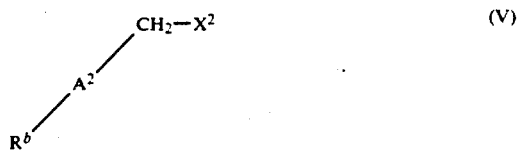

(V)

wherein $R^b$ is as defined in relation to formula (IV) and $X^2$ is a halogen atom, with a compound of formula (VI):

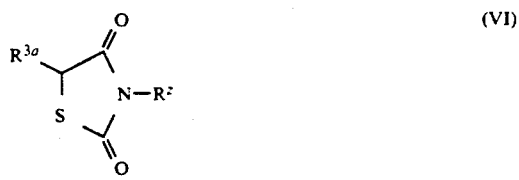

(VI)

wherein $R^{3a}$ represents hydrogen, an alkyl, aralkyl or aryl group and $R^z$ is as defined in relation to formula (III); and thereafter if required, converting a moiety $R^b$ into a moiety $R^a$.

The reaction between the compounds of formula (V) and (VI) may be carried out in any suitable solvent, such as 1,2-dimethoxyethane, at any temperature providing a convenient rate of formation of the required product, suitably at ambient temperature and preferably in the presence of a base such as an alkali metal base, for example potassium amide in liquid ammonia.

Suitably, $X^2$ represents a chlorine atom.

A compound of formula (V) may be prepared from a compound of formula (VII):

(VII)

wherein $A^2$ and $R^b$ are as defined in relation to formula (IV), by reaction of the compound of formula (VII) with a halogenating reagent.

Suitable halogenating agents are conventional halogenating agents, for example when $X^2$ represents a chlorine atom, a suitable halogenating agent is thionyl chloride.

The conditions for the reaction between the compound of formula (VII) and the halogenating agent will of course depend largely upon the nature of the particular halogenating agent chosen, but the conditions are generally the conventional conditions appropriate to the particular halogenating agent used, for example suitable conditions when the halogenating agent is thionyl chloride involve the use of methylene chloride or chloroform as solvent and at low to medium temperature for example a reaction temperature of between 0° and 30° C.

The compounds of formula (IV), (V) and (VII) are generally known commercially available compounds or are prepared using methods analogous to those used to prepare such compounds.

Suitable protecting groups in any of the abovementioned reactions are those used conventionally in the art for example those disclosed in 'Protective Groups in Organic Synthesis', Wiley Interscience, 1981, T. W. Greene. Thus, for example, a suitable nitrogen protecting group is a benzyl group or a benzyloxycarbonyl group and a suitable hydroxyl or thiol protecting group is a benzyl group or a p-methoxybenzyl group.

The methods of formation and removal of such protecting groups are those conventional methods appropriate to the molecule being protected and includes those methods disclosed in the abovementioned 'Protective Groups in Organic Synthesis'.

A compound of formula (I), or a tautomeric form thereof, and/or a pharmaceutically acceptable salt thereof and/or a pharmaceutically acceptable solvate thereof, may also be prepared by reacting a compound of formula (VIII):

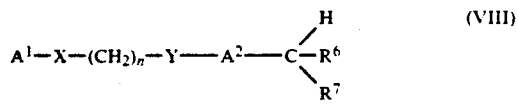

wherein $A^1$, $A^2$, X, Y and n are as defined in relation to formula (I), $R^6$ represents hydrogen and $R^7$ represents a halogen atom or $R^6$ together with $R^7$ represents an oxo group, with a compound of formula (IX):

wherein $R^8$ represents hydrogen or a group $R^{3a}$, as defined in relation to formula (VI), and $R^z$ is as defined in relation to formula (III), providing that $R^8$ represents only hydrogen when $R^6$ together with $R^7$ in compound (VIII) represent an oxo group and providing that $R^8$ represents only the group $R^{3a}$ and $R^z$ represents only a protecting group when $R^6$ represents hydrogen and $R^7$ represents a halogen atom; and thereafter if required carrying out one or more of the following optional steps:

(i) converting a compound of formula (I) into a further compound of formula (I);

(ii) removing any protecting group;

(iii) preparing a pharmaceutically acceptable salt of a compound of formula (I) and/or a pharmaceutically acceptable solvate thereof.

When $R^6$ and $R^7$ in the compound of formula (VIII) together represent an oxo group and $R^8$ in the compound of formula (IX) represents hydrogen, the reaction between the compounds of formulae (VIII) and (IX) may conveniently be carried out under analogous conditions to those described above for the reaction between compounds of formulae (IV) and thiazolidine-dione. When $R^6$ represents hydrogen and $R^7$ represents a halogen atom in the compound of formula (VIII) and $R^8$ represents $R^{3a}$ in the compound of formula (IX), then the reaction between the compounds of formulae (VIII) and (IX) may be carried out using analogous conditions to those in the reaction between the compounds of formulae (V) and (VI).

When $R^7$ represents a halogen atom, it is favourably a chlorine atom.

A compound of formula (VIII), when $R^6$ together with $R^7$ represent an oxo group, may be prepared by reacting a compound of formula (X):

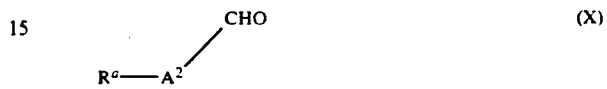

wherein $A^2$ is as defined in relation to formula (I) and $R^a$ is as defined in relation to formula (III), with an appropriate reagent capable of converting $R^a$ into a moiety of the above defined formula (b).

Suitably $R^a$ represents -YH.

When $R^a$ represents a hydroxyl group or a thiol group in the compound of formula (X) (or a compound of formula (III)), a particularly appropriate reagent is a compound of formula (XI):

wherein $A^1$, X and n are as defined in relation to a compound of formula (I) and $R^d$ represents a displaceable group.

Suitable displaceable groups include leaving groups or atoms or groups or atoms convertible into leaving groups or atoms.

Suitable leaving groups or atoms include mesyl or tosyl groups and halogen atoms such as chlorine or bromine atoms.

Suitable groups convertible into leaving groups include hydroxy groups.

Preferably, when X represents $-NR^1$, $R^d$ represents a hydroxyl group.

The reaction between the compound of formula (X) (or a compound of formula (III)) wherein $R^a$ is a hydroxyl group and the reagent of the above defined formula (XI) may suitably be carried out in an aprotic solvent, such as tetrahydrofuran, at low to medium temperature, for example at ambient temperature, and preferably in the presence of a coupling agent such as that provided by triphenylphosphine and diethyl azodicarboxylate.

The reaction between the compound of formula (X) (or a compound of formula (III)) wherein $R^a$ is a hydroxyl group or a thiol group, and the reagent of the abovedefined formula (XI) may be carried out in an aprotic solvent, such as dimethylformamide, at a low to elevated temperature, for example in the range of from 50° C. to 120° C. and preferably in the presence of a base, such as sodium hydride.

The reagent of formula (XI) may be prepared by reacting a compound of formula (XII):

wherein $A^1$ and X as defined in relation to formula (I), with a compound of formula (XIII):

$$R^d\text{-}(CH_2)_n\text{-}R^e \quad \text{(XIII)}$$

wherein $R^d$ is as defined in relation to formula (XI) and $R^e$ represents $R^d$ or a group $OR^f$ wherein $R^f$ is hydrogen or a hydroxyl protecting group; and thereafter where necessary removing any protecting group.

Suitably, $R^d$ represents a halogen atom such as a chlorine or a bromine atom.

The reaction between the compounds of formulae (XII) and (XIII) may be carried out in any suitable solvent, such as ethanol at any temperature providing a convenient rate of formation of the required product, such as a temperature in the range of from 30° C. to the reflux temperature of the solvent.

In one alternative aspect, a compound of formula (XI) when X represents $NR^1$, n is 2 and $R^d$ is a hydroxyl, mesyl or tosyl group may be prepared by reacting a compound of the above defined formula (XII) with epoxyethane and thereafter if required converting the hydroxyl group to the mesyl or tosyl group.

The reaction between the compound of formula (XI) and epoxyethane may be carried out in any suitable solvent, such as toluene at any temperature providing a convenient rate of formation of the required product, such as a temperature in the range of from 0° to 30° C.

The compounds of formula (VI) and (IX) are known available compounds or they may be prepared according to methods used to prepare such compounds, for example those methods disclosed in DE 3045059.

The compounds of formula (X) are known compounds or they are compounds prepared by methods analogous to those used to prepare known compounds, for example 4-hydroxybenzaldehyde is a known commercially available compound and 4-mercaptobenzaldehyde may be prepared as outlined in Beilstein 8.I.533.

Conveniently, the compounds of formula (XI) wherein $R^d$ represents a mesyl or tosyl group may be prepared from the corresponding compound wherein $R^d$ is a hydroxy group, by means of known mesylation or tosylation methods.

The compounds of formula (XI) wherein X represents O or S and n represents 2 are either commercially available, as for example are those wherein $R^d$ represents chlorine, bromine or a hydroxy group and $A^1$ is phenyl.

When X represents $NR^1$ in the compounds of formula (III) or (X), a suitable value for $R^a$ is a group $A^1\text{-}NR^1\text{-}CO\text{-}(CH_2)_{n-1}\text{-}Y\text{-}$ wherein $A^1$, $R^1$, Y and n are as defined in relation to formula (I), but especially when n represents 2.

The group $A^1\text{-}NR^1\text{-}CO\text{-}(CH_2)_{n-1}\text{-}Y\text{-}$ may be converted into a moiety of the abovedefined formula (b) by conventional reducing methods, for example by using complex metal hydride reduction using such as lithium aluminiium hydride in an aprotic solvent, such as tetrahydrofuran, at any temperature providing a convenient rate of formation of the required product, suitably at an elevated temperature for example at the reflux temperature of the solvent, and where appropriate in an inert atmosphere.

When $R^a$ represents a group $A^1\text{-}NR^1\text{-}CO\text{-}(CH_2)_{n-1}\text{-}Y\text{-}$, a suitable value for $R^b$ is a group of formula $X^3\text{-}CO\text{-}(CH_2)_{n-1}\text{-}Y\text{-}$ wherein Y and n are as defined in relation to formula (I), but preferably n is 2, and $X^3$ represents a halogen atom, preferably a chlorine atom.

A suitable reagent for converting a group $X^3\text{-}NR^1\text{-}CO\text{-}(CH_2)_{n-1}\text{-}Y\text{-}$ into $A^1\text{-}NR^1\text{-}CO\text{-}(CH_2)_{n-1}\text{-}Y\text{-}$ is a compound of formula (XIIA)

$$A^1\text{-}NR^1H \quad \text{(XIIA)}$$

wherein $A^1$ and $R^1$ are as defined in relation to formula (I).

Reaction conditions are conventional conditions appropriate to the reacting compounds: Thus a compound of formula (X), wherein X represents the abovedefined group $A^1\text{-}NR^1\text{-}CO\text{-}(CH_2)_{n-1}\text{-}Y\text{-}$ may be prepared by reacting a compound of formula (IVA):

$$X^3\text{—}CO\text{—}(CH_2)_{n-1}\text{—}Y\text{——}A^2\text{——}CHO \quad \text{(IVA)}$$

wherein $A^2$, $X^3$, Y and n are as defined above, with a compound of the abovedefined formula (XIIA).

Preferably, the —CHO group of the compound of formula (IVA) is in protected form. Formation and removal of the protected —CHO group being effected by conventional reagents and procedures.

The reaction between compounds of formulae (IVA) and (XIIA) may be carried out in an inert solvent, such as benzene, at any temperature providing a convenient rate of formation of the required product, suitably at an elevated temperature, such as the reflux temperature of the solvent.

A compound of formula (IVA) may be prepared by halogenation of a compound of formula (IVB):

$$HO_2C\text{—}(CH_2)_{n-1}\text{—}Y\text{——}A^2\text{——}CHO \quad \text{(IVB)}$$

wherein $A^2$, Y and n are as defined above, but preferably n is 2.

The halogenation of (IVB) may be carried out using conventional halogenation procedures, for example by the use of a thionyl halide in an inert solvent such as benzene.

In the halogenation of (IVB) the —CHO group is generally transformed into a dihalomethyl group. In our hands this was a suitable protected form of the —CHO group as preferred in the reaction between compound of formula (IVA) with the compound of formula (XIIA). The —CHO group is suitably regenerated by hydrolysis with a mild base suitably by treatment with an aqueous solution of an amine, for example hexamine, at an elevated temperature, conveniently the reflux temperature of the solvent.

A compound of formula (VIII) wherein $R^6$ represents hydrogen and $R^7$ represents a halogen atom, may be prepared by reacting a compound of formula (XIV):

$$A^1\text{—}X\text{—}(CH_2)_n\text{—}Y\text{——}A^2\text{——}CH_2OH \quad \text{(XIV)}$$

wherein $A^1$, $A^2$, X, Y and n are as defined in relation to formula (I), with a halogenating agent.

Suitable halogenating agents are conventional halogenating agents, for example when $R^7$ represents a chlorine atom, a suitable halogenating agent is thionyl chloride.

The conditions for the reaction between the compound of formula (XIV) and the halogenating agent will of course depend largely upon the nature of the particular halogenating agent chosen, but the conditions are generally the conventional conditions appropriate to the particular halogenating agent used, for example suitable conditions when the halogenating agent is thionyl chloride involve the use of methylene chloride or chloroform as solvent and at low to ambient temperature, for example a reaction temperature of between 0° and 30° C.

A compound of formula (XIV) may be prepared by reacting a compound of formula (XV):

wherein $A^2$ and $R^a$ are as defined in relation to formula (III), with an appropriate reagent capable of converting a moiety $R^a$ into a moiety of the above defined formula (b).

The nature of the moiety $R^a$, the nature of the appropriate reagent and suitable reaction conditions for the reaction between the compound of formula (XV) and the appropriate reagent are as described above for the reaction between a compound of formula (III) and the appropriate reagent.

Where necessary a compound of formula (XV) may be prepared from a compound of the abovedefined formula (VII), by converting a moiety $R^b$ into a moiety $R^a$, using methods hereinbefore described.

The abovementioned conversion of a compound of formula (I) into a further compound of formula (I) includes the following conversions:

(a) reducing a compound of formula (I) wherein $R^2$ and $R^3$ together represent a bond, to a compound of formula (I) wherein $R^2$ and $R^3$ each represent hydrogen;

(b) converting one group $R^1$ into another group $R^1$; and (c) converting a compound of formula (I) wherein $R^3$ represents hydrogen into a compound of formula (I) wherein $R^3$ represents an alkyl, aralkyl or aryl group.

The conversion of a compound of formula (I) into a further compound of formula (I) may be carried out by using any appropriate conventional procedure.

A suitable reduction method for the abovementioned conversion (a) includes catalytic reduction or the use of a metal/solvent reducing system.

Suitable catalysts for use in the catalytic reduction are palladium on carbon catalysts, preferably a 10% palladium on charcoal catalyst; the reduction being carried out in a solvent, for example dioxan, suitably at ambient temperature.

Suitable metal/solvent reducing systems include magnesium in methanol.

The abovementioned reduction of a compound of formula (III) wherein $R^2$ and $R^3$ together represent a bond to a compound of formula (III) wherein $R^2$ and $R^3$ each represent hydrogen, may be carried out under analogous conditions to those referred to above in conversion (a) of the compound of formula (I).

In the abovementioned conversion (b), suitable conversions of one group $R^1$ into another group $R^1$ includes converting a group $R^1$ which represents hydrogen into a group $R^1$ which represents an acyl group.

The conversion of a compound of formula (I) wherein $R^1$ represents hydrogen into a compound of formula (I) wherein $R^1$ represents acyl may be carried out using any appropriate conventional acylation procedure, such as by treating an appropriately protected compound of formula (I) with an acylating agent. For example acetic anhydride may be used to prepare the compound of formula (I) wherein $R^1$ is acetyl.

In the abovementioned conversion (c), a compound of formula (I) wherein $R^3$ represents hydrogen may be converted into a compound of formula (I) wherein $R^3$ represents an alkyl, aralkyl or aryl group by reacting the appropriate compound of formula (I) with a compound of formula (XVI):

wherein $R^{3a}$ represents an alkyl, aralkyl or an aryl group and $X^2$ represents a halogen atom, such as a chlorine atom.

The reaction between the appropriate compound of formula (I) and the compound of formula (XVI) may be carried out in any suitable solvent, such as 1,2-dimethoxyethane, at any temperature providing a convenient rate of formation of the required product, suitably at ambient temperature, and preferably in the presence of a base such as an alkali metal base, for example potassium amide in liquid ammonia.

It will be appreciated that in the abovementioned conversions (a), (b) and (c) any reactive group in the compound of formula (I) may be protected where necessary, according to conventional chemical practice.

Where appropriate the isomeric forms of the compounds of formula (I) and the pharmaceutically acceptable salts thereof may be prepared as individual isomers using conventional chemical procedures.

The compounds of formula (III), (VIII) and (XIV) are believed to be novel compounds and as such form a further aspect of the invention.

The compounds of formula (XII), (XIII), (XV) and (XVI) are known commercially available compounds or they may be prepared according to methods analogous to those used to prepare known compounds.

As mentioned above the compounds of the invention are indicated as having useful therapeutic properties: The present invention accordingly provides a compound of formula (I), or a tautomeric form thereof and/or a pharmaceutically acceptable salt thereof and/or a pharmaceutically acceptable solvate thereof, for use as an active therapeutic substance.

Thus the present invention provides a compound of formula (I), or a tautomeric form thereof and/or a pharmaceutically acceptable salt thereof and/or a pharmaceutically acceptable solvate thereof, for use in the treatment of and/or prophylaxis of hyperglycaemia.

In a further aspect the present invention also provides a compound of formula (I), or a tautomeric form thereof and/or a pharmaceutically acceptable salt thereof and/or a pharmaceutically acceptable solvate thereof, for use in the treatment and/or prophylaxis of hyperlipidaemia.

As indicated hereinbefore the present invention also provides a compound of formula (I) or a tautomeric form thereof and/or a pharmaceutically acceptable salt thereof and/or a pharmaceutically acceptable solvate thereof for use in the treatment of hypertension, cardiovascular disease and certain eating disorders.

A compound of formula (I), or a tautomeric form thereof and/or a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a compound of the general formula (I), or a tautomeric form thereof, or a pharmaceutically acceptable salt thereof, or a pharmaceutically acceptable solvate thereof, and a pharmaceutically acceptable carrier therefor.

As used herein the term 'pharmaceutically acceptable' embraces compounds, compositions and ingredients for both human and veterinary use: for example the term 'pharmaceutically acceptable salt' embraces a veterinarily acceptable salt.

The composition may, if desired, be in the form of a pack accompanied by written or printed instructions for use.

Usually the pharmaceutical compositions of the present invention will be adapted for oral administration, although compositions for administration by other routes, such as by injection and percutaneous absorption are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant.

Typical carriers include, for example, microcrystalline cellulose, starch, sodium starch glycollate, polyvinylpyrrolidone, polyvinylpolypyrrolidone, magnesium stearate, sodium lauryl sulphate or sucrose.

Most suitably the composition will be formulated in unit dose form. Such unit dose will normally contain an amount of the active ingredient in the range of from 0.1 to 1000 mg, more usually 0.1 to 500 mg, and more especially 0.1 to 250 mg.

The present invention further provides a method for the treatment and/or prophylaxis of hyperglycaemia in a human or non-human mammal which comprises administering an effective, non-toxic, amount of a compound of the general formula (I), or a tautomeric form thereof and/or a pharmaceutically acceptable salt thereof and/or a pharmaceutically acceptable solvate thereof to a human or non-human mammal in need thereof.

The present invention further provides a method for the treatment of hyperlipidaemia and/or hypertension and/or cardiovascular disease and/or certain eating disorders in a human or non-human mammal, which comprises administering an effective, non-toxic, amount of a compound of formula (I), or a tautomeric form thereof and/or a pharmaceutically acceptable salt thereof and/or a pharmaceutically acceptable solvate thereof, to a human or non-human mammal in need thereof.

Conveniently, the active ingredient may be administered as a pharmaceutical composition hereinbefore defined, and this forms a particular aspect of the present invention.

In the treatment and/or prophylaxis of hyperglycaemia in humans, and/or the treatment and/or prophylaxis of hyperlipidaemia in humans, the compound of the general formula (I), or a tautomeric form thereof and/or a pharmaceutically acceptable salt thereof and/or a pharmaceutically acceptable solvate thereof, may be taken in doses, such as those described above, one to six times a day in a manner such that the total daily dose for a 70 kg adult will generally be in the range of from 0.1 to 6000 mg, and more usually about 1 to 1500 mg.

In the treatment and/or prophylaxis of hyperglycaemia in non-human mammals, especially dogs, the active ingredient may be administered by mouth, usually once or twice a day and in an amount in the range of from about 0.025 mg/kg to 25 mg/kg, for example 0.1 mg/kg to 20 mg/kg. Similar dosage regimens are suitable for the treatment and/or prophylaxis of hyperlipidaemia in non-human mammals.

The dosages regimens for the treatment of hypertension, cardiovascular disease and eating disorders will generally be those mentioned above in relation to hyperglycaemia.

In a further aspect the present invention provides the use of a compound of formula (I), or a tautomeric form thereof and/or a pharmaceutically acceptable salt thereof and/or a pharmaceutically acceptable solvate thereof, for the manufacture of a medicament for the treatment and/or prophylaxis of hyperglycaemia.

The present invention also provides the use of a compound of formula (I), or a tautomeric form thereof and/or a pharmaceutically acceptable salt thereof, and/or a pharmaceutically acceptable solvate thereof, for the manufacture of a medicament for the treatment and/or prophylaxis of hyperlipidaemia, hypertension, cardiovascular disease or certain eating disorders.

The following Procedures and Examples illustrate the invention but do not limit it in any way.

PROCEDURE 1

4-[2-Phenoxyethoxy]benzaldehyde

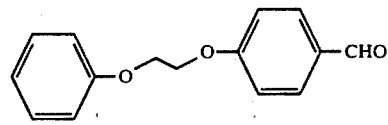

4-Hydroxybenzaldehyde (7.4 g) was dissolved in dry dimethylformamide (200 ml) and sodium hydride (2.42 g; 60% dispersion in oil) was added portionwise. After stirring under nitrogen for one hour at room temperature, a solution of γ-bromophenetole (12.16 g) in dry dimethylformamide (50 ml) was added and the reaction mixture was heated overnight at 80° C. The mixture was cooled and excess solvent evaporated off. The residue was added to 10% sodium hydroxide solution and extracted with ethyl acetate (3×200 ml). The combined organic extracts were washed with 10% sodium hydroxide solution (200 ml), water (2×200 ml), brine (2×200 ml) dried (MgSO$_4$,) filtered and evaporated to dryness to give the title product.

$^1$H NMRδ(CDCl$_3$)

4.35 (4H, s); 6.9–7.4 (7H, complex); 8.9 (2H, d); 10.0 (1H, s).

PROCEDURE 2

4-[(N-Methyl-N-phenylamino)carbonylmethoxy]benzaldehyde

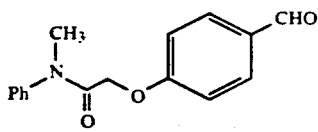

(i) Thionyl chloride (36.7 g, 22.5 ml) was added dropwise to a stirred, ice-cooled suspension of 4-carboxymethoxybenzaldehyde (9.00 g) in dry benzene (100 ml) containing pyridine (2.5 ml). The resulting mixture was heated at reflux for 2 hours, then cooled and the solvent evaporated. The residue containing impure 4-(dichloromethyl)phenoxyacetyl chloride was used in the next stage of the procedure without further purification.

(ii) A solution of N-methylaniline (5.44 g, 5.5 ml) in dry benzene (100 ml) was added dropwise to a stirred suspension of the acid chloride (part (i) above) in benzene (100 ml). The resulting mixture was heated at reflux for 16 hours, then cooled and the solvent evaporated. The residue was dissolved in N,N-dimethylformamide (120 ml) at 60° C., and a solution of hexamine (8.4 g) in water (100 ml) added. The mixture was heated at reflux and stirred vigorously for 1 hours, cooled and diluted with water (1l), acidified with dilute hydrochloric acid and extracted with ethyl acetate (3×300 ml). The combined organic solutions were washed with water (4×1l) and the brine (1l), dried (MgSO4) and evaporated. The resulting gum was chromatographed on silica gel with 1% methanol in dichloromethane to afford the title compound, mp 97-100<C.

$^1$H NMR (CDCl$_3$)

3.22 (3H, s); 4.50 (2H, s); 6.80 (2H, d); 6.90-7.80 (7H, complex); and 9.75 (1H, s).

PROCEDURE 3

4-[2-(N-Methyl-N-phenylamino)ethoxy]benzyl alcohol.

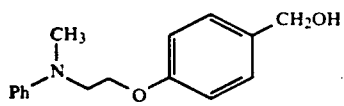

A solution of 4-[N-Methyl-N-phenylamino)carbonylmethoxy]-benzaldehyde (8.25 g) in dry tetrahydrofuran (300 ml) was added dropwise to a mechanically stirred, ice-cooled slurry of lithium aluminium hydride (5.90 g) in dry tetrahydrofuran (100 ml) under a nitrogen atmosphere. The resulting mixture was heated at reflux for 9 hours and then cooled in ice and cautiously quenched by the addition of water (6 ml), sodium hydroxide solution (10% w/v, 6 ml) and water (18 ml). After being refluxed for a further 30 minutes, the mixture was filtered through a Soxhlet thimble and the residue extracted with refluxing tetrahydrofuran for 3 hours. The solvent was evaporated and the residue chromatographed on silica gel with 1.5% methanol in dichloromethane as solvent to yield the title compound as an oil.

$^1$H NMR (CDCl$_3$)

1.80 (1H,s, exchanges with D$_2$O); 3.10 (3H,s); 3.75 (2H,t); 4.15 (2H,t); 4.60 (2H,s); and 6.70-7.40 (9H, complex).

PROCEDURE 4

4-[2-(N-Methyl-N-phenylamino)ethoxy]benzaldehyde

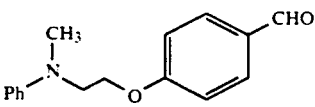

A mixture of 4-[2-(N-methyl-N-phenylamino)ethoxy]benzyl alcohol (3.36 g), manganese (IV) oxide (11.3 g) and dichloromethane (150 ml) were stirred at room temperature overnight. The mixture was filtered through a Soxhlet thimble and the residue extracted with refluxing dichloromethane for 2.5 hours. The solvent was evaporated to afford the title compound, an oil, which was used without further purification.

$^1$H NMR (CDCl$_3$) 3.10 (3H,s); 3.80 (2H,t); 4.27 (2,t); 6.70-7.50 (7H, complex); 7.90 (2H, d); and 10.00 (1H,s).

EXAMPLE 1

5-[4-2-Phenoxyethoxy)benzylidene]-2,4-thiazolidinedione

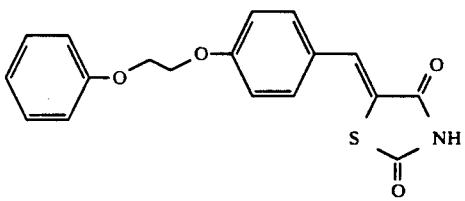

A solution of 4-[(2-phenoxyethoxy]benzaldehyde (14.2 g) and 2,4-thiazolidinedione (7.9 g) in toluene (400 ml) containing a catalytic amount of piperidiniumacetate was boiled under reflux in a Dean and Stark apparatus for 2 hours. The mixture was cooled and filtered and the filtered solid was dried to give the title compound (mp 223° C.).

$^1$H NMRδ(DMSO-d$_6$) 4.35 (4H,s); 6.9-7.75 (10 H, complex); 12.0 ($^1$ H, broad s, exchanges with D$_2$O).

EXAMPLE 2

5-[4-(2-Phenoxyethoxy)benzyl]-2,4-thiazolidinedione

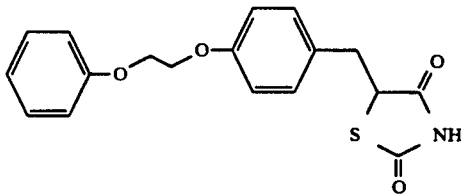

5-[4-(2-Phenoxyethoxy)benzylidene]-2,4-thiazolidinedione (4 g) in dry 1,4-dioxan (200 ml) was reduced under hydrogen in the presence of 10% palladium on charcoal (8 g) at ambient temperature and atmospheric pressure until hydrogen uptake ceased. The solution was filtered through diatomaceous earth, the filter pad was washed exhaustively with dioxan and the combined filtrates were evaporated to dryness under vacuum. The title compound (mp 133° C.) was obtained after crystallisation from methanol.

$^1$H NMRδ(DMSO-d$_6$) 3.0-3.4 (2H, complex); 4.3 (4H, s); 4.85 (1H, complex); 6.9-7.35 (9H, complex); 12.0 (1H, broad s, exchanges with D$_2$O).

EXAMPLE 3

5-(4-[2-N-Methyl-N-phenylamino)ethoxy]benzylidene)-2, 4-thiazolidinedione.

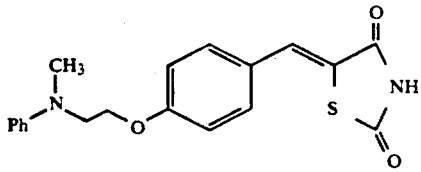

A mixture of 4-[2-(N-methyl-N-phenylamino)ethoxy]-benzaldehyde (2.99 g), 2,4-thiazolidinedione (1.50 g), piperidine (0.18 ml) and benzoic acid (0.18 g) were heated at reflux in toluene (250 ml) in a Dean and Stark apparatus for 3.5 hours. The mixture was cooled and the resulting solid filtered off, washed with cold toluene an dried under vacuum to afford the title compound. mp 162°-163° C.

$^1$H NMR (CDCl$_3$:DMSO-d$_6$1:1) 3.05 (3H,s); 3.72 (2H,t); 4.20 (2H,t); 6.50-7.80 (10 H, complex); and 12.40 (1H, br s, exchanges with D$_2$O).

EXAMPLE 4

5-(4-[2-(N-Methyl-N-phenylamino)ethoxy]benzyl-2,4-thiazolidinedione.

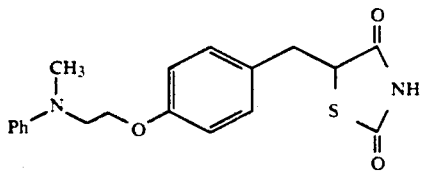

5-(4-[2-(N-Methyl-N-phenylamino)ethoxy]benzylidene)-2,4-thiazolidinedione (3.2 g) was suspended in dioxan (300 ml) and hydrogenated over 10% palladium-charcoal (3.4 g) for 7.25 hours at room temperature and pressure. A further portion of catalyst (3.4 g) was added, and reduction continued for a total of 48 hours. The reaction mixture was filtered through diatomaceous earth and the solvent evaporated. The resulting gum was chromatographed on silica gel with 1% methanol in dichloromethane to afford the title compound as a low-melting foam.

$^1$H NMR (CDCl$_3$) 3.00 (3H,s); 3.05 (1H,dd); 3.37 1H,dd); 3.70 (2H,t); 4.15 (2H,t); 4.47 (1H,dd); 6.65-7.40 (9H, complex); and 9.00 (1H, br s, exchanges with D$_2$O).

EXAMPLE 5

5(4-[2-(N-Methyl-N-phenylamino)ethoxy]benzyl)-2,4-thiazolidinedione, sodium salt.

Sodium hydride (60% dispersion in oil; 0.27 g) was added to a stirred, ice-cooled solution of 5-(4-[2-(N-Methyl-N-phenylamino)ethoxy]benzyl-2,4-thiazolidinedione (2.39 g) in methanol (10 ml). The mixture was stirred for 5 minutes at 0° C., then filtered. The resulting solid was washed with dry diethyl ether and dried under vacuum at 40° C. The title compound darkens at 270° C., and decomposes above 290° C.

$^1$H NMR (DMSO-d$_6$) 2.58 (1H.dd); 2.96 (3H,s); 3.31 (1H,dd); 3.69 (2H,t); 4.07 (3H, complex); and 6.55-7.45 (9H, complex).

DEMONSTRATION OF EFFICACY OF COMPOUNDS

Obese Mice, Oral Glucose Tolerance Test

C57bl/6 obese (ob/ob) mice were fed on powdered oxoid diet. After at least one week, the mice continued on a powdered oxoid diet or were fed powered oxoid diet containing the test compound. After 8 days on the supplemented diet all of the mice were fasted for 5 hours prior to receiving an oral load of glucose (3 g/kg). Blood samples for glucose analysis were taken 0, 45, 90 and 135 minutes after glucose administration and the results appear below as the percentage reduction in area under the blood glucose curve where test compound treated groups are compared with the control groups. 7 mice were used for each treatment.

| EXAMPLE NO: | LEVEL IN DIET (μmol kg$^{-1}$ of DIET) | % REDUCTION IN AREA UNDER BLOOD GLUCOSE CURVE |
|---|---|---|
| 2 | 300 | 19 |
| 5 | 300 | 48 |

Toxicology

No toxicological effects were indicated for any of the compounds of the invention in any of the abovementioned tests.

We claim:

1. A compound of formula (I):

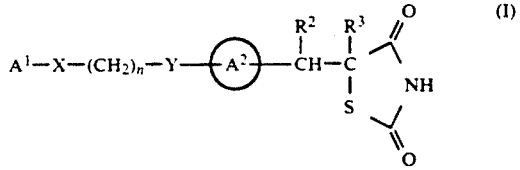

or a tautomeric form thereof and/or a pharmaceutically acceptable salt thereof, and/or a pharmaceutically acceptable solvate thereof, wherein:

A$^1$ represents a substituted or unsubstituted aryl group;

A$^2$ represents a benzene ring having in total up to five substituents;

X represents O, S or NR$^1$ wherein R$^1$ represents a hydrogen atom, an alkyl group, an acyl group, an aralkyl group, wherein the aryl moiety may be substituted or unsubstituted, or a substituted or unsubstituted aryl group;

Y represents O or S;

R$^2$ represents hydrogen;

R$^3$ represents hydrogen or an alkyl, aralkyl or aryl group or R$^2$ together with R$^3$ represents a bond; and n represents an integer n the range of from 2 to 6; alkyl groups being selected from C$_{1-12}$ alkyl groups; and aryl groups being selected from phenyl and naphthyl groups optionally substituted with up to five substituents selected from halogen, alkyl, phenyl, alkoxy, haloalkyl, hydroxy, amino, nitro, carboxy, alkoxycarbonyl, alkoxycarbonylalkyl, alkylcarbonyloxy, and alkylcarbonyl.

2. A compound according to claim 1, wherein $A^1$ represents a phenyl group.

3. A compound according to claim 1, wherein $R^2$ represents hydrogen and $R^3$ represents an alkyl group.

4. A compound according to claim 1, wherein $R^2$ and $R^3$ each independently represent hydrogen.

5. A compound according to claim 1, wherein $A^2$ represents a moiety of formula (a):

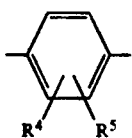

(a)

wherein $R^4$ and $R^5$ each independently represent hydrogen, halogen, substituted or unsubstituted alkyl or alkoxy.

6. A compound according to claim 5, wherein $R^4$ and $R^5$ each independently represent hydrogen, halogen, alkyl or alkoxy.

7. A compound according to claim 1, wherein X is O and Y is O.

8. A compound according to claim 1, of formula (II):

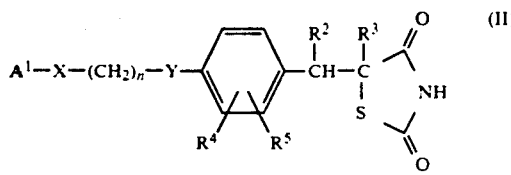

(II)

or a tautomeric form thereof, and/or a pharmaceutically acceptable salt thereof and/or a pharmaceutically acceptable solvate thereof, wherein $A^1$, X, Y, $R^2$, $R^3$ and n are as defined in relation to formula (I) in claim 1 $R^4$ and $R^5$ each independently represent hydrogen, halogen, substituted or unsubstituted alkyl or alkoxy.

9. A compound according to claim 1, being:
5-[4-(2-phenoxyethoxy)benzylidene]-2,4-thiazolidinedione; or
5-[4-(2-phenoxyethoxy)benzyl]-2,4-thiazolidinedione;
or a tautomeric form thereof and/or a pharmaceutically acceptable salt thereof, and/or a pharmaceutically acceptable solvate thereof.

10. A pharmaceutical composition comprising a compound of the general formula (I), as defined in claim 1, or a tautomeric form thereof, or a pharmaceutically acceptable salt thereof, or a pharmaceutically acceptable solvate thereof, and a pharmaceutically acceptable carrier therefor.

11. A method for the treatment and/or prophylaxis of hyperglycaemia in a human or non-human mammal which comprises administering an effective, non-toxic, amount of a compound of the general formula (I), as defined in claim 1, or a tautomeric form thereof and/or a pharmaceutically acceptable salt thereof and/or a pharmaceutically acceptable solvate thereof to a human or non-human mammal in need thereof.

12. A method for the treatment of hyperlipidaemia in a human or non-human mammal, which comprises administering an effective, non-toxic, amount of a compound of formula (I), as defined in claim 1 or a tautomeric form thereof and/or a pharmaceutically acceptable salt thereof and/or a pharmaceutically acceptable solvate thereof, to a human or non-human mammal in need thereof.

* * * * *